United States Patent [19]

Kessler

[11] Patent Number: 5,169,455
[45] Date of Patent: Dec. 8, 1992

[54] METHOD FOR SIMULTANEOUSLY CLEANING AND DISINFECTING CONTACT LENSES

[76] Inventor: Jack H. Kessler, 23 Carriage House Path, Ashland, Mass. 01721

[21] Appl. No.: 866,904

[22] Filed: Apr. 10, 1992

Related U.S. Application Data

[63] Continuation-in-part of Ser. No. 771653, Oct. 4, 1991.

[51] Int. Cl.$^5$ .................... B08B 3/04; A61K 37/48
[52] U.S. Cl. ........................................ 134/42; 422/1;
422/28; 424/94.4; 424/613; 424/616;
252/DIG. 12; 252/174.12
[58] Field of Search ............... 134/42; 422/1, 28;
424/94.4, 613, 616; 252/DIG. 12, 174.12

[56] References Cited

U.S. PATENT DOCUMENTS

| Re. 32,672 | 5/1988 | Huth et al. | 252/DIG. 14 |
| 3,910,296 | 10/1975 | Karageozian et al. | 134/42 |
| 4,588,586 | 5/1986 | Kessler et al. | 435/264 |
| 5,055,287 | 10/1991 | Kessler | 424/94.4 |

FOREIGN PATENT DOCUMENTS 05695 9/1986 World Int. Prop. O. .

Primary Examiner—Theodore Morris
Assistant Examiner—Zeinab El-Arini

[57] ABSTRACT

A method for the simultaneous cleaning and disinfecting of contact lenses based upon the combined use of a proteolytic enzyme for cleaning and a peroxidative enzymatic reaction with donor and acceptor molecules and a thiol agent for color control.

6 Claims, No Drawings

METHOD FOR SIMULTANEOUSLY CLEANING AND DISINFECTING CONTACT LENSES

BACKGROUND

This application is a continuation in part of U.S. patent application Ser. No. 771,653 filed Oct. 4, 1991.

This invention teaches the combined use of a proteolytic enzymatic reaction to hydrolyze adsorbed proteins and a peroxidative enzymatic reaction to disinfect contact lenses simultaneously in one step.

Contact lens wearers must both disinfect and clean their contact lenses. Disinfection is required to preclude the potential of eye infection from microbes; cleaning is required to prevent or remove the accumulation of proteinaceous materials from the surface of contact lenses which irritates the eye, reduces light transmission and increases light refraction.

A wide number of chemical and physical methods have been used to disinfect contact lenses. There are no commercially available cold chemical disinfection formulations which are (1) effective against robust microbes, such as fungi and or viruses; are (2) ocularly non-irritating; and which will (3) simultaneously clean the lens. U.S. Pat. No. 4,588,586 issued to Kessler, et. al. describes the use of the enzyme peroxidase to generate biocidal agents via an enzymatic reaction with donor and acceptor molecules. The preferred source of acceptor molecules is hydrogen peroxide at a concentration which, of itself, will not function as an effective biocidal agent against robust microbes. In fact, this chemistry causes the rapid reduction of the majority of hydrogen peroxide to water during the disinfecting reaction. Instead of using hydrogen peroxide as the biocidal agent, this system relies upon the enzymatic reaction of peroxidase to generate biocidal agents which function as a bactericide. In U.S. Pat. No. 4,937,072 issued to Kessler, on Jun. 20$^{th}$, 1990 it was further discovered that when a source of iodide ions is selected as the donor molecule the peroxidase actuated reaction is effective against all pathogens including fungi, viruses and spores.

It is well known in the art that proteinaceous materials adsorb to hydrophilic contact lenses during normal wear. Gross mechanical cleansing of contact lenses comprised of materials other than glass and polymethyl-methacrylate (PMMA) is neither practical nor effective. Proteins bind so tightly to some lipophilic surfaces that traditional cleaning approaches using surface active agents (detergents and/or surfactants) are not effective.

Lenses comprised of organosiloxane-methacrylate, hydroxyethylmethacrylate, vinylpyrrolidone, hydroxyethylmethylmethacrylate, glycerolmethacrylate, polysiloxane/methylmethacrylate copolymers and monomers which when polymerized absorb more than 35% water are not compatible with the use of mechanical cleaning methods to remove adsorbed proteins.

The marketplace has accepted the use of proteolytic enzymes to hydrolyze the amide bonds of proteins adsorbed to the surface of contact lenses. These adsorbed proteins are ultimately broken down into much smaller polypeptides and possibly amino acids. Unlike adsorbed proteins, the polypeptides resulting from proteolysis partition into the contact lens matrix and aqueous environment. U.S. Pat. No. 3,910,296 discloses the use of proteases for cleaning contact lenses.

U.S. Pat. No. Re. 32,672 describes a method to simultaneously clean and disinfect contact lenses using proteolytic enzymes and a disinfecting concentration of hydrogen peroxide. For this type of process to be effective, the hydrogen peroxide must be of a sufficient concentration to act as a bacteriocidal agent at the initiation of the disinfection process and must maintain a sufficient concentration to act as a bacteriostatic agent at the conclusion of the process.

None of these disclosure teach or contemplate the use of a proteolytic enzyme for cleaning a contact lens in combination with the enzyme peroxidase for disinfecting the lens via an enzymatic reaction. One skilled in the art would expect that such a proteolytic enzyme would be expected to rapidly inactivate peroxidase via proteolysis thereby vitiating the disinfection process. Unexpectedly, by combining in one solution a peroxidase enzyme and a proteolytic enzyme it has been found that contact lenses may be simultaneously cleaned and disinfected.

Iodide ions are essential to the composition for generating a useful disinfective species. However, the use of iodide ions in an effective concentration range induces a concomitant coloration which is easily discerned by human eye and which discolors certain types of contact lenses particularly those comprised of polyvinylpyrrolidone. In accordance with the present invention, the change in color may be controlled without effecting the cleaning action of the protease through the addition of a thiol containing agent. The thiol containing agent should be added after the enzymatic reaction has been initiated and a sufficient period of time has elapsed to allow the reduction of at least about 50 percent of the initial concentration of hydrogen peroxide and/or the oxidation of at least 25 percent of the iodide ions. Time release coatings are commonly used to effect a sequential dissolution of pilled agents and are suitable for use with this invention.

SUMMARY OF THE INVENTION

This invention describes a method to simultaneously disinfect and clean contact lenses using an aqueous environment minimally comprised of peroxidase, peroxide, iodide, and a proteolytic enzyme; said method is comprised of contacting the lenses with a solution comprised of (1) a disinfecting composition of peroxidase, iodide and hydrogen peroxide with the concentration of hydrogen peroxide at a level that is insufficient to cause complete disinfection of robust microbes in and of itself; (2) an effective amount of a composition of a proteolytic enzyme sufficient to remove protein accretions from the lenses; and (3) an effective amount of a thiol agent for controlling the color of the solution substantially independent of the action of the proteolytic enzyme wherein said thiol agent is added after the reduction of at least about 50 percent of the initial concentration of hydrogen peroxide and/or the oxidation of at least 25 percent of the iodide ions.

SPECIFIC EMBODIMENTS

The peroxidase of this invention is identified by the International Union of Biochemistry and the International Union of Pure and Applied Chemistry by the Enzyme Commission identification No. E.C. 1.11.1.7. Peroxidase can be obtained from a wide variety of sources. The least expensive and most robust peroxidase suitable for this application is horseradish peroxidase although lactoperoxidase can also be used. It is anticipated that new sources and types of peroxidases will become available with the current tools available in the field of molecular biology i.e. cloned enzymes. Such enzymes should be considered to fall within the scope of this invention. Commercially obtained peroxidase comes lyophilized as a dry powder. Alternatively, peroxidase can be dissolved in a suitable carrier for future admixture in the disinfecting/cleaning aqueous environment.

The concentration of peroxidase in this application is 0.00005 to 0.5 mg/ml. The preferred concentration is 0.005 to 0.05 mg/ml. Higher concentrations of peroxidase offer the advantage of increased product shelf-life and greater insensitivity to proteolysis.

The donor molecule of this invention is iodide. Suitable sources of iodide for this invention include sodium iodide and potassium iodide as well as other salts of iodide. Any compound which yields iodide ions upon dissolution in water, without yielding other deleterious effects to the proteolytic or peroxidative activity of the system, is suitable for this application. The simple salts of iodide have the advantage of low cost and extended stability.

The initial concentration of iodide ion required at the start of the peroxidase reaction in this application is 0.05 to 0.8 mg/ml. The preferred range of iodide anions in this application is 0.1 to 0.35.

The oxidant of this invention is a compound which yields a peroxide dissolution in an aqueous environment or hydrogen peroxide formulated directly into a liquid product. Alternatively methyl peroxide can be formulated in the product.

The initial concentration of hydrogen peroxide required at the start of the peroxidase reaction in this application is 0.0001 to 0.03% weight to volume. The preferred range of hydrogen peroxide in this application is 0.001 to 0.005% weight to volume at the start of the disinfecting peroxidase reaction.

Disinfecting reactions which are based upon the use of hydrogen peroxide as the biocidal agent must substantially maintain the initial concentration of hydrogen peroxide that is formulated in these products. Product which use peroxide as a biocide all have a high concentration of hydrogen peroxide which remains in solution upon completion of disinfection and therefore require a procedure to eliminate the hydrogen peroxide so that it does not cause eye irritation. In contrast to peroxide based products, the concentration of hydrogen peroxide at the start of the disinfecting reaction using this chemistry is at least two times, and often as much as ten to fifty times, the concentration of hydrogen peroxide at the conclusion of the disinfecting reaction. This is because hydrogen peroxide is being catalytically reduced to water by the action of the enzyme peroxidase. That is, peroxide is not the biocidal agent but merely acts to accept electrons from iodide ions.

Suitable materials which can serve as precursors for hydrogen peroxide include metal peroxides, percarbonates, persulphates, perphosphates, peroxyesters, alkali metal persulfates, urea peroxide, peroxyacids, alkylperoxides, diperisophthalic acid, peroxydiphosphate salts, acylperoxides and perborates. Hydrogen peroxide and the sodium salts of perborates and persulfates are most preferred. Mixtures of two or more of these substances can also be used. A single concentration range for all of the possible sources of peroxide cannot be stated since the active oxygen concentration varies significantly between peroxides.

A disinfecting combination of peroxidase, iodide and peroxide means any combination of these components in an aqueous environment which, when present with a effective cleaning concentration of proteolytic enzyme, cause a six log inactivation of Staphlococcus aureus within 30 minutes. The preferred time for a disinfection combination of peroxidase, iodide and peroxide to effect disinfection is 2 to 10 minutes.

The proteolytic enzymen(s) used in this invention should have the ability to remove adsorbed protein accretions from the contact lenses via proteolytic action causing said proteolytic protein byproducts to be dissolved in the surrounding aqueous environment. Such enzyme(s) have been documented to have associated lipolytic and/or amylolytic activity. For instance, collagenase can be categorized into more than eight different classes depending upon its 1) specific activity, 2) relative level of non-specific proteases and 3) level of clostripain.

A variety of proteases can be used to remove adsorbed proteinaceous material. These proteases include trypsin, collaginases, keratinase, elastase, aminopeptidases, carboxylase, pancreatin, pronases, and subtilisins. Current commercial products employ the serine protease subtilisin. These proteins are well known in the art and are available from commercial sources in various stats of purity.

The amount of proteolytic enzyme require to effect cleaning will depend upon the specific activity of the enzyme, its substrate specificity, and the amount of time allowed for treatment. As a general rule the working solution should contain 0.001 to 1.0 Anson units of activity per single lens treatment. Concentrations lower than this can be used but will require significant periods of time to clean the lens.

Color is controlled by the addition of a thiol containing agent after the enzymatic reaction has effected a reduction of at least about 50 percent of the initial concentration of hydrogen peroxide and/or the oxidation of at least 25 percent of the iodide ions. Thiol containing agents such as sodium thiosulfate, dithiothreitol, dithioerythritol, dithiobenzoic acid, cystamine and other thiol containing agents which will be familiar to one skilled in the art are suitable for use with this invention. The concentration of the thiol containing agent will vary with the thiol agent selected. The concentration range for thiols will vary between 0.1 and 0.001%.

Other additives are typically added to the formulation including effervescing agents, buffering agents, binders, lubricants, excipients, and the like. The exact mix of additives depends upon whether the product is to be delivered as a liquid or a powder and upon the exact product configuration that is selected. Other color control additives, such as sorbic acid, may also be added for use in conjunction with the thiol agent.

A prerequisite for the storage of any formulation is the prevention of peroxidase, iodide and hydrogen peroxide, the three components responsible for disinfection, from combining under conditions wherein the catalytic process is initiated thereby allowing the depletion of said components. If the peroxidase, iodide and peroxide components are permitted to interact before intended for sterilization, the inevitable depletion of the enzyme's substrate molecules (peroxide and iodide) will result and thereby attenuate the effectiveness of the formulation. In addition, if the proteolytic enzyme and peroxidase are stored in a fashion such that the protease can hydrolyze peroxidase, then the disinfective activity of the formulation will be vitiated.

The decolorizing thiol agent can be added at a minimal concentration to control color. The decolorizing thiol agent can be added in solution or solid form after the disinfection has occurred. Alternatively, the thiol decolorizing agent can be added in the form of a time released component which is timed to become effective or to reach its maximum effectiveness only after oxidation of at least 25% of the iodide ions and preferably after 50% of the iodide ions. The oxidation of at least 25% of the iodide ions corresponds to an enzymatic reduction of about 50% of the initial hydrogen peroxide concentration.

It is acceptable to combine any two of the three disinfecting components (peroxide source, iodide and peroxidase) of this system and isolate them from the third component in order to effect this end so long as the proteolytic enzyme cannot hydrolyze peroxidase.

It is also possible to store the components of this system in a powder or pill form such that both enzymatic reactions are precluded until such time as said powder or pill is admixed in a suitable carrier. If a powder or pill is desired for use in an application where it is required to actively maintain a sterile environment for a defined period of time it is possible to add a formulation wherein iodide and enzyme dissolve rapidly and peroxide is release slowly over time.

It is possible to incorporate certain components of a formulation into more than one component such that some components may effectively be released after a defined period of time or over a defined period of time. This will have the effect of preventing the interaction of one component with another during table preparation, product storage, and the subsequent product use. Agents responsible for eliminating or removing residual components of or byproducts from the cleaning and disinfecting formulation may require a release into the environment after a defined period of time. For instance, decolorizers may be incorporated into a two pill system so as to be released after disinfection has been completed. Specifically, sodium thiosulfate could be incorporated into a time released pill to prevent the colorization of lenses.

To practice this invention, a solution of peroxidase, iodide, peroxide, proteolytic enzyme and other additives is prepared and the lenses contacted with this solution, preferably by being immersed in this solution. The lenses will be left in contact with such solution long enough so that substantially all protein is removed from the lenses surfaces and the lenses are disinfected. As per the preferred ranges described above the disinfection process is usually more rapid than the cleaning process. There is no preferred sequence of addition of the components except that the three components responsible for disinfection should be added at the same time. In any event, peroxidase should not be incubated with the proteolytic enzyme prior to adding the iodide and peroxide.

The following examples illustrate, but do not define the limits of, the scope of the invention.

EXAMPLES

1) Stock solutions of; 1) bacterial protease type VIII (Sigma Catalog No. P-5380); 2) bacterial protease from *Streptomyces griseus* type XIV (Sigma Catalog No. P-5147); 3) pancreatin as contained in OPTI-ZYME enzymatic cleaner (Alcon); 4) subtilisin as contained in the Soft Mate Enzyme Plus Cleaner (Barnes/Hind); 5) papain as contained in Allergan's Enzymatic Cleaner; and 6) pepsin (Boehringer Mannheim Gmblt Cat. No. 106-057) were prepared.

The stock solutions for OPTI-ZYME, Soft Mate Enzyme Plus Cleaner, and Allergan's Enzymatic Cleaner were prepared as per the manufacturer's recommended reconstitution volume.

The stock solutions for the proteolytic enzymes bacterial protease type VIII, bacterial protease from *Streptomyces griseus* type XIV, and pepsin were reconstituted at a concentration of 0.05 mg/ml in normal saline and also contained: 5 mMolar sodium borate, 0.015 mg/ml polyethylene glycol, 0.075 mg/ml tartaric acid, 0.025 ethylenediamintetracetate. The stock solutions were brought to a pH of 7.8.

Horseradish peroxidase was prepared as a stock solution at 5 mg/ml which contained 5 mg/ml sodium iodide. A stock solution of *Staphlococcus aureus* (ATCC 8739) at a concentration of $10^8$ colony forming units per ml (cfu) was prepared and stored in a refrigerator until required for use. A stock solution of hydrogen peroxide was prepared at a concentration of 0.1% (w/v). A stock solution of sodium thiosulfate was prepared which contained 5.0% sodium thiosulfate, 0.04% sodium borate and 0.40% boric acid.

Six Hydrocurve ® contact lenses were coated with protein by placing the lenses into a phosphate buffered saline solution at pH 7.0 which contained 1 mg/ml of egg white lysozyme and then heating the lenses for 60 minutes at 90° C. After the lenses were cooled they were rubbed between thumb and finger after rinsing with preservative free isotonic sterile saline (Ross Laboratories).

Protein coating of the lenses was determined by examination of the convex surface under a microscope. Protein coating was scored based upon optical estimates of what percentage of the convex surface was coated by protein. After the treatment described in the first paragraph, all lenses were found to have 100% of their convex surface covered by a protein coating.

Five mls of the proteolytic enzymes bacterial protease type VIII, bacterial protease from *Streptomyces griseus* type XIV, and pepsin were added (concentration equal to 0.4 mg/ml in normal saline) to clean plastic containers. Five mls of the stock solution of OPTI-ZYME Soft Mate Enzyme Plus Cleaner, and Allergan's Enzymatic Cleaner was added to clean plastic containers. Each solution was placed into two clean plastic containers and a protein coated contact lens was placed into each container.

Immediately after the contact lenses were placed into each plastic container, the following material was added: 50 microliters of the stock solution of hydrogen peroxide; 350 microliters of the stock solution of peroxidase, 50 microliters of the *Staphlococcus aureus* stock solution.

The lenses were soaked for 6 hours and then 200 microliters of the stock sodium thiosulfate solution was added to each container and allowed to incubate at room temperature for 15 minutes. A 100 microliter aliquot from each container was spread onto blood agar plates and incubated at 37° C. overnight to screen for bacterial growth. Each lens was rinsed in saline (Boil-'n-Soak; Alcon Laboratories) and the percentage of protein which remained absorbed to the lenses was determined by visual inspection under the microscope.

The percentage of the protein which was removed ranged between 25 and 40% for the OPTI-ZYME, Soft Mate Enzyme Plus Cleaner, and Allergan's Enzymatic Cleaner. The percentage of the protein which was removed ranged between 10 and 20% for the bacterial protease type VIII, bacterial protease type XIV, and pepsin. No bacterial growth was observed in any of the samples. No lenses displayed any coloration upon visual examination under the microscope.

The enzymatic activity of horseradish peroxidase was monitored every thirty minutes during the cleaning/disinfection reaction by determining the amount of time required to generate a visually discernable precipitate in 50 mMolar phosphate-citrate buffer with sodium perborate (Sigma Catalog No. C-4922) using 4-chloro-1-naphthol as substrate (Sigma Catalog No. C-6788). Peroxidase dramatically activity diminished during the course of the reactions with bacterial protease type VIII and bacterial protease type XIV. The time required to generate a visually discernable precipitate increased by 10 fold.

2) Eighteen Hydrocurve ® contact lenses were coated with protein by placing the lenses into a phosphate buffered saline solution at pH 7.0 which contained 1 mg/ml of egg white lysozyme and then heating the lenses for 60 minutes at 90° C. After the lenses were cooled they were rubbed between thumb and finger after rinsing with perservative free isotonic sterile saline (Ross Laboratories).

Protein coating of the lenses was determined by examination of the convex surface under a microscope. Protein coating was scored based upon optical estimates of what percentage of the convex surface was coated by protein. After the treatment described in the first paragraph, all lenses were found to have 100% of their convex surface covered by a protein coating.

The lenses were placed in a Barnes/Hind plastic contact lens holders (SOFT MATE Hydra-Mat II cleaning and storage unit) and the lens holder was filled with isotonic sterile saline (Ross Laboratories) to the line to insure that once the top was added the lens would be covered with saline.

A powdered mixture which contained a disinfecting formulation of peroxidase, hydrogen peroxide and sodium iodide was added to the saline solution. The disinfecting powdered formulation was comprised of 2 mg of peroxidase, 0.5 mg of sodium perborate and 2.5 mg of sodium iodide. To the saline solution one SOFT MATE Enzyme Plus cleaner tablet was added. The Soft Mate Enzyme Plus Cleaner (Barnes/Hind) contains the enzyme subtilisin. The top of the SOFT MATE Hydra-Mat II cleaning and storage unit was replaced on the chamber and the top was slowly rotated several times to thoroughly mix the contents.

The protein coated contact lens was soaked for eight hours. The amount of protein removal was determined by visual examination under a microscope. The process described above was repeated using the commercially available cleaning pills called 1) the OPTI-ZYME enzymatic cleaner (Alcon Laboratories) which contains the enzyme pancreating and 2) the Enzymatic Cleaner (Allergan, Inc.) which contains the enzyme papain. The results of these measurements are shown below in Table 1. The values in Table I represent the average of two trials.

The percent surface cleaned equaled the percentage of the surface not covered by a protein film. Two types of controls were run (1) the same process was repeated for a second contact lens in the absence of the peroxidase enzyme and (2) the same process was repeated for a second contact lens in the absence of sodium thiosulfate.

Bactericidal activity was measured by aliquoting 100 microliters of the solution which contained the contact lens of interest onto the surface of a "Blood Agar Plate", pipeting the 100 microliters with a sterile loop, incubating at 37° C. for 48 hours, and visually inspecting the plates for bacterial growth. If no growth was detected, then complete disinfection was judged to have been effected. No bacterial growth was observed in any of the samples.

Coloration the lenses was determined by examination of the convex surface under a microscope. Coloration was judged to be either discernable or not discernable based upon visual examination of the lens. No lenses treated with thiosulfate displayed any coloration upon visual examination under the microscope. Lenses which were not treated with thiosulfate displayed coloration although the coloration did slowly dissipate over the course of 20 to 60 minutes after the lenses were placed into sterile saline.

TABLE I

| Conditions | Disinfection +peroxidase | Disinfection −peroxidase | % Surface Cleaned |
|---|---|---|---|
| OPTI-ZYME | yes +thiol (no color) | no +thiol (no color) | ≈80 |
|  | yes −thiol (color) | — | 85 |
| Enzymatic Cleaner (Alcon) | yes +thiol (no color) | no +thiol (no color) | ≈80 |
|  | yes −thiol (color) | — | 70 |
| Soft Mate Enzyme | yes +thiol (no color) | no +thiol (no color) | ≈95 |
|  | yes −thiol (no color) | — | 88 |

3) A Hydrocurve ® contact lens was coated with protein by placing the lens into a phosphate buffered saline solution at pH 7.0 which contained 1 mg/ml of egg white lysozyme and then heating the lens for 60 minutes at 90° C. After the lens was cooled it was rubbed between thumb and finger after rising with preservative free isotonic sterile saline.

Protein coating of the lenses was determined by examination of the convex surface under a microscope. The lens was found to have 100% of its convex surface covered by a protein coating.

The lens was placed in a Barnes/Hind plastic contact lens holders (SOFT MATE Hydra-Mat II cleaning and storage unit) and the lens holder was filled with isotonic sterile saline to the line to insure that once the top was added the lens would be covered with saline.

A powdered mixture which contained a disinfecting formulation of peroxidase, hydrogen peroxide and sodium iodide was added to the saline solution. The disinfecting powdered formulation was comprised of 1 mg of peroxidase, 0.35 mg of sodium perborate and 3.5 mg of sodium iodide. One SOFT MATE Enzyme Plus cleaner tablet was added to the saline solution. The top of the SOFT MATE Hydra-Mat II cleaning and storage unit was replaced on the chamber and the top was slowly rotated several times to thoroughly mix the contents.

The protein coated contact lens was soaked for one hour. Ten microliters of a suspension of the enzyme catalase isolated from bovine liver with a specific activity of 40,000 units per milligram and a concentration of 5 mg/ml was added to the cleaning and storage unit.

The reaction was allowed to incubate for an additional 5 minutes to insure that the overwhelming majority of hydrogen peroxide was eliminated.

The contact lens was highly colored after the catalase incubation and a drop of a saturated sodium thiosulfate solution was added to the solution. After 10 minutes the lens was examined for color. No color was visibly detected. This experiment indicates that the effect of thiosulfate with this chemistry is directed to the elimination and or removal of colored species and not directed to the reduction of hydrogen peroxide.

What is claimed is:

1. A method for the simultaneous cleaning and disinfecting of contact lenses which method comprises contacting the lenses with an aqueous solution comprised of (1) a disinfecting composition consisting essentially of peroxidase, iodide and hydrogen peroxide with the concentration of peroxide being insufficient to function, of itself, as a bacteriocidal agent for said solution, (2) an effective amount of a proteolytic enzyme sufficient to remove protein accretions from said lenses, and (3) an effective amount of a thiol agent for controlling the color of the solution substantially independent of the cleaning action of said proteolytic enzyme with the introduction of said thiol agent being effective only after oxidation of at least 25 percent of the iodide ions said thiol agent is selected from the group consisting of: sodium thiosulfate, dithiothreitol, dithioerythritol, dithiobenzoic acid and cystamine.

2. A method as defined in claim 1 wherein said peroxide concentration is between 0.0001 to 0.03% weight to volume upon contact with said lenses.

3. A method as defined in claim 2 wherein the initial concentration of iodide ions is between 0.05–0.8 mg/ml.

4. A method as defined in claim 3 wherein said effective amount of said thiol agent is between 0.001 and 0.1%.

5. A method as defined in claim 4 wherein said thiol agent is time released in said solution to reach maximum effectiveness after oxidation of at least 25% of the iodide ions.

6. A method as defined in claim 3 wherein said thiol agent is introduced only after oxidation of at least 50% of the iodide ions.

* * * * *